US008095390B2

(12) United States Patent
Bluemler et al.

(10) Patent No.: US 8,095,390 B2
(45) Date of Patent: Jan. 10, 2012

(54) MEDICAL TREATMENT SYSTEM WITH A DEVICE FOR SUPPLYING PATIENT-RELATED DATA

(75) Inventors: Holger Bluemler, Bad Homburg (DE); Pia Daniel, Bodmann (DE); Elmar Enders, Niederwern (DE); Marco Graefe, Bad Homburg (DE); Martin Gruendken, Rosbach (DE); Gerhard Schumacher, Butzbach (DE); Thomas Stahl, Esselbach (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 538 days.

(21) Appl. No.: 11/921,625

(22) PCT Filed: Apr. 29, 2006

(86) PCT No.: PCT/EP2006/004049
§ 371 (c)(1),
(2), (4) Date: Jun. 9, 2008

(87) PCT Pub. No.: WO2006/128536
PCT Pub. Date: Dec. 7, 2006

(65) Prior Publication Data
US 2009/0037216 A1 Feb. 5, 2009

(30) Foreign Application Priority Data
Jun. 3, 2005 (DE) .......................... 10 2005 025 516

(51) Int. Cl.
G06Q 50/00 (2006.01)

(52) U.S. Cl. ................................ 705/3; 705/2; 210/739
(58) Field of Classification Search .................. 705/2–4; 604/4.01; 210/739, 143, 645, 646
See application file for complete search history.

(56) References Cited

U.S. PATENT DOCUMENTS

| 5,788,851 | A  | * | 8/1998  | Kenley et al. ................. 210/739 |
| 6,188,407 | B1 |   | 2/2001  | Smith et al. |
| 7,044,927 | B2 | * | 5/2006  | Mueller et al. ............... 604/4.01 |
| 2004/0220832 | A1 | | 11/2004 | Moll et al. |

FOREIGN PATENT DOCUMENTS

| DE | 10 2004 011 264 | 9/2004 |
| EP | 1195708 | 4/2002 |
| WO | WO 01/37899 | 5/2001 |
| WO | WO 01/65463 | 9/2001 |
| WO | WO 02/093312 | 11/2002 |

OTHER PUBLICATIONS

International Search Report for PCT/EP2006/004049.
English translation of the International Preliminary Report on Patentability for PCT/EP2006/004049.

* cited by examiner

Primary Examiner — Gerald J. O'Connor
Assistant Examiner — Michelle Le
(74) Attorney, Agent, or Firm — Kenyon & Kenyon LLP

(57) ABSTRACT

The invention relates to a medical treatment system, which has at least one device for carrying out a medical treatment, in particular dialysis treatment and a device for providing patient-related data. The patient-related data is stored by the server and the data can be displayed in a patient mode on a screen. The dialysis system has various security features, which prevent an erroneous input and the erroneous display of patient-related data in the patient mode on the screen.

32 Claims, 18 Drawing Sheets

MEDICAL TREATMENT SYSTEM WITH A DEVICE FOR SUPPLYING PATIENT-RELATED DATA

FIELD OF THE INVENTION

The present invention relates generally to a medical treatment system with at least one device for carrying out a medical treatment and a device for supplying patient-related data, as well as, in particular, an extracorporeal blood treatment system, specifically a dialysis system with at least one dialysis device and a device for supplying patient-related data.

BACKGROUND OF THE INVENTION

DE 10 2004 011 264 A1 discloses a plurality of patient stations incorporated with a central server, so that the treatment of each patient can be monitored and adjusted from one doctor's station. A dialogue between the doctor's station and the individual patient stations is possible via the data network. Further interconnected dialysis systems are known from EP 1195708 A1 and WO 2001/37899 A2.

A common feature of the dialysis systems of the prior art is that patient-related data that can be loaded from the individual treatment devices are supplied on a central server. In addition, patient-related data that are fed into the treatment device can be stored on the central server.

Because of the stringent safety requirements in medical engineering, very high safety demands are imposed on the data transfer between the treatment devices and the server in order to eliminate both operating errors and malfunctions of the medical treatment system.

SUMMARY OF THE INVENTION

One aspect of the present invention is a medical treatment system, in particular a dialysis system, which provides the operator with comprehensive information on the medical treatment, and safely eliminates input errors and malfunctions.

The input/display device of the present invention is designed so that machine-related data sets are displayed in a treatment mode and patient-related data sets are displayed in a patient mode. "Machine related data sets" are defined as all data that relate to the machine control system, for example the feed rates of the blood and dialyzing fluid pump, the ultrafiltration rate, etc. "Patient-related data sets" are defined as all data that has no influence on the control of the treatment device and serve only as information for the operator.

The input/display device of the medical treatment system according to the present invention is characterized by a plurality of means for entering and displaying different groups of patient-related data. Each means for entering and displaying a group of patient-related data exhibits means for displaying a plurality of data sets and means for selecting one or more data sets from the plurality of data sets. It is therefore possible to select the data sets required for the treatment from predetermined data sets without having to enter the data sets each time. Moreover, each means for entering and displaying a group of patient-related data exhibits means for displaying one or more of the selected data sets. It is therefore possible to automatically document the data sets selected during treatment for an operator.

In one embodiment, the input/display device is designed as a touch screen for entering and displaying the patient-related data, wherein the means for entering and displaying the different groups of patient-related data are pages that can be represented on the screen, containing fields that can be individually selected.

The data transfer takes place between the treatment device and a device for supplying patient-related data that has a facility for storing patient-related data. A group of patient-related data may, for example, incorporate a plurality of data sets that provide the operator information on the type and execution of the treatment. For example, information on the medications administered during the treatment, or medications prescribed for the treatment, as well as results obtained and actions initiated during treatment can be provided. This patient-specific data can be individually displayed to an operator.

In a further embodiment of the medical treatment system, different groups of patient-related data can be selected from a plurality of data sets, and means for inputting one or more data sets, which can be assigned to the selected data sets and displayed, are provided. An operator is therefore able to enter additional information relating, for example, to the method of treatment and treatment process, the medications administered, and the results obtained and actions initiated, so that this information is available to an operator in subsequent treatments. At least some of the data sets selected can preferably be stored with the storage device, so that the data sets are permanently available to an operator.

In patient mode, a patient-related display area is preferably only defined for displaying patient-related data sets. This display area serves exclusively to inform the operator about the patients, but does not allow control of the treatment device. In a preferred embodiment, the patient-related display area forms part of the screen of the treatment device, and can be designed as a touch screen.

When data are transferred from the device for supplying the patient-related data to the individual treatment devices there is a risk that the data sets may not be fully represented. To avoid operating errors or incorrect information the input/display device is provided with means for determining whether a patient-related data set can be represented within the limits of the patient-related display area without overlapping a data set already displayed, thereby preventing the data sets from being displayed if the limits are exceeded or overlap. This ensures that an operator is not provided with only partial information, which could result in incorrect conclusions.

The medical treatment system is also characterised by means for cyclic interrogation of patient-related data which indicate when new patient-related data are supplied from the device for supplying the patient-related data. If only machine-related data sets are displayed in the treatment mode, the operator is still informed of the presence of new patient-related data. The operator may then call up the patient mode to display the patient-related data sets and process them if necessary.

BRIEF DESCRIPTION OF THE DRAWINGS

An embodiment of the information is described in greater detail with reference to the drawings.

DETAILED DESCRIPTION OF THE DRAWINGS

Figure 1:
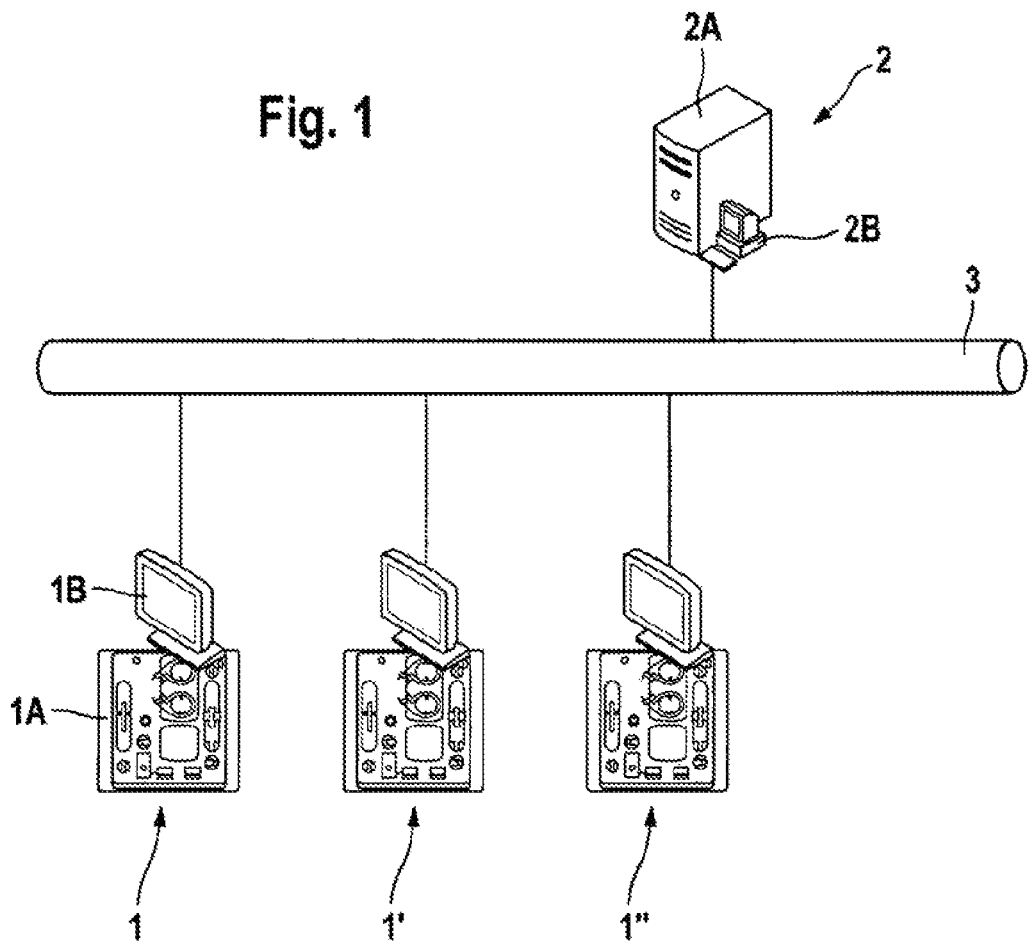
FIG. 1 shows an extracorporeal blood treatment system in a simplified, diagrammatic representation.

FIG. 1 shows the essential components of an extracorporeal blood treatment system, in particular a hemodialysis system, in a highly simplified diagrammatic representation. The dialysis system incorporates a plurality of dialysis devices, 1, 1', 1" and a device 2 for supplying patient-related data, which are connected to each other by a network 3.

The device for supplying the patient-related data 2, for example, a server, is provided with a device 2A for storing the patient-related data, e.g., a hard disk memory, and a device 2B for entering the patient-related data, for example, a PC with screen and keyboard.

The individual dialysis devices 1, 1', 1" are each provided with a machine part 1A and an input/display device 1B. The input/display device is a screen preferably designed as a touch screen with which both machine-related data for controlling the dialysis device and patient-related data can be entered and displayed. Machine part 1A of the dialysis device exhibits a central control unit for controlling the individual machine components.

Figure 2:
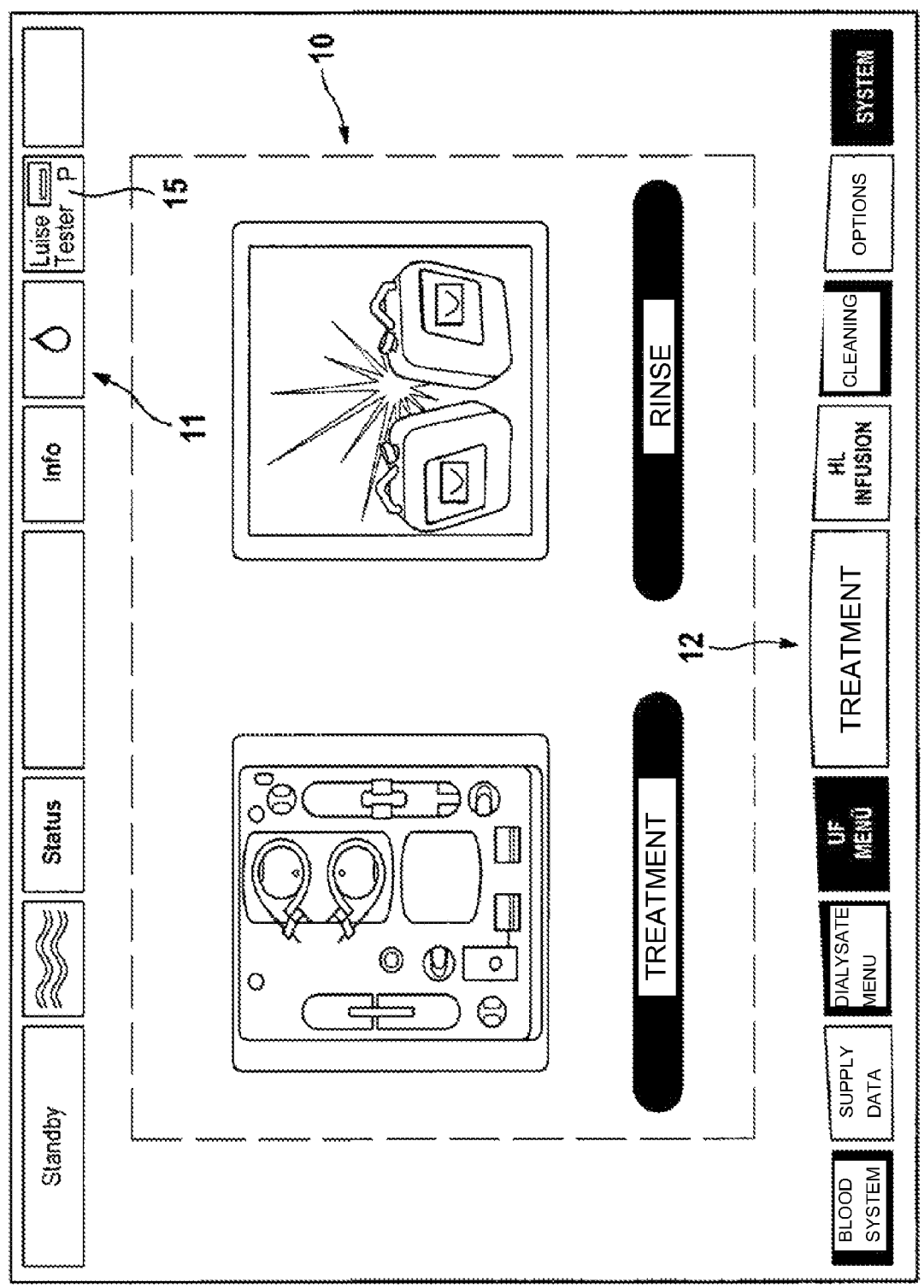
FIG. 2 shows the screen surface of the treatment device in treatment mode.

FIG. 2 shows the screen surface of screen 1A of dialysis device 1. The screen surface is divided into a central display region 10 and a status bar 11, which can be located at the upper edge of the screen, and a menu bar 12, which can be located at the lower edge of the screen. The limits of the central area 10 are represented by dotted lines in FIG. 2. Status bar 11 and menu bar 12 each exhibit a plurality of selectable fields or buttons that can be selected with the finger or a cursor.

The operator may select either the treatment mode or the patient mode on the screen. FIG. 2 shows the treatment mode in which machine-related data can be entered and displayed. In this mode, for example, the parameters predetermined for the treatment can be entered for the central control unit of the dialysis device.

The patient mode, in which patient-related data can be entered and displayed on the screen, represents a function that is fully independent of the treatment mode. Inputs and displays in the patient mode therefore have no influence on the dialysis treatment and serve as information and documentation only.

The input and display of patient-related data in the patient mode takes place within the central display range 10, so that status bar 11 and menu bar 12, together with the left and right display areas 13, 14, in which further machine-related data, e.g. the arterial and venous blood pressure and the blood flow, can be represented, remain visible.

The patient-related data are loaded from server 2 of the dialysis system. Since the data are supplied centrally, changes and adaptations to customer requirements are possible and can quickly be made. In the patient mode, dynamic, interactive program sequences may take place which are not stored in the dialysis device but are loaded from the server. Since the program sequences in the dialysis device run in isolation from the machine control, they cannot influence the medical function of the dialysis device.

The interactive program sequences serve to represent the patient-related data on the screen in patient mode, e.g. laboratory data. Moreover, inputs by the operator are also possible. As a reaction to the inputs, the server can transmit further data to the dialysis device, thereby allowing specific user guidance.

The interactivity of the program sequences is achieved by screen pages which are loaded dynamically from the server and whose structure follows a page description language. Communication between the dialysis device and the server takes place with the protocol HTTP or HTTPS, the content of the pages being described in HTML. The page descriptions contain information on the control elements to be displayed on the screen, their attributes, where they are positioned, and how they are to react to user inputs.

The simplest form of a program sequence is the representation of a screen page generated by the server, with none or very few possibilities of data input by the operator. This page is selected via a menu point, for example, and closed by means of a button.

A complex program sequence may contain a sequence of screen pages whose order and content are established according to operator inputs. Interactive help or training pages whose sequence is controlled by the buttons are examples of this.

An even more complex program sequence enables patient-related data inputs to be received in the server using data which are made available elsewhere, e.g. from a dialysis data bank or by measured data acquisition from the dialyzer itself, in order to execute a calculation algorithm and therefore calculate medically relevant parameters which may be relevant to the present or future treatments of the patient.

The function of the screen in the patient mode is explained in greater detail below with reference to examples.

At predetermined intervals, the dialysis device asks the server cyclically whether new patient-related data is available. If this is the case, a patient button 15 bearing the name of the patient flashes in status bar 11 of the screen if the treatment mode, not the patient mode, is activated. The patient mode does not open until the operator selects the patient button 15. In any case, it is ensured that the operator is informed of all the safety-relevant data at all times.

Figure 3:
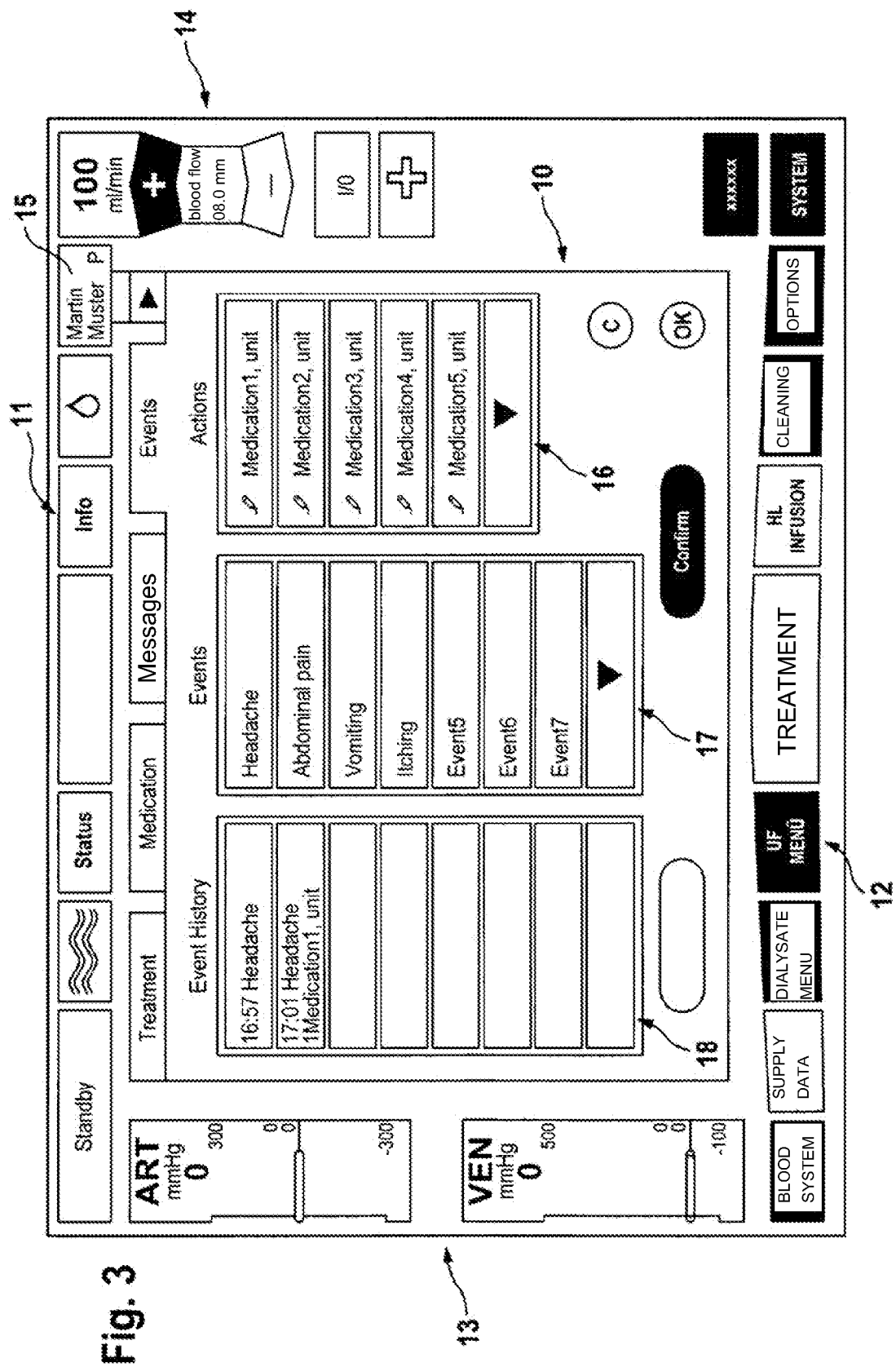
FIG. 3 shows the screen surface of the treatment device in patient mode.
Figure 4A:
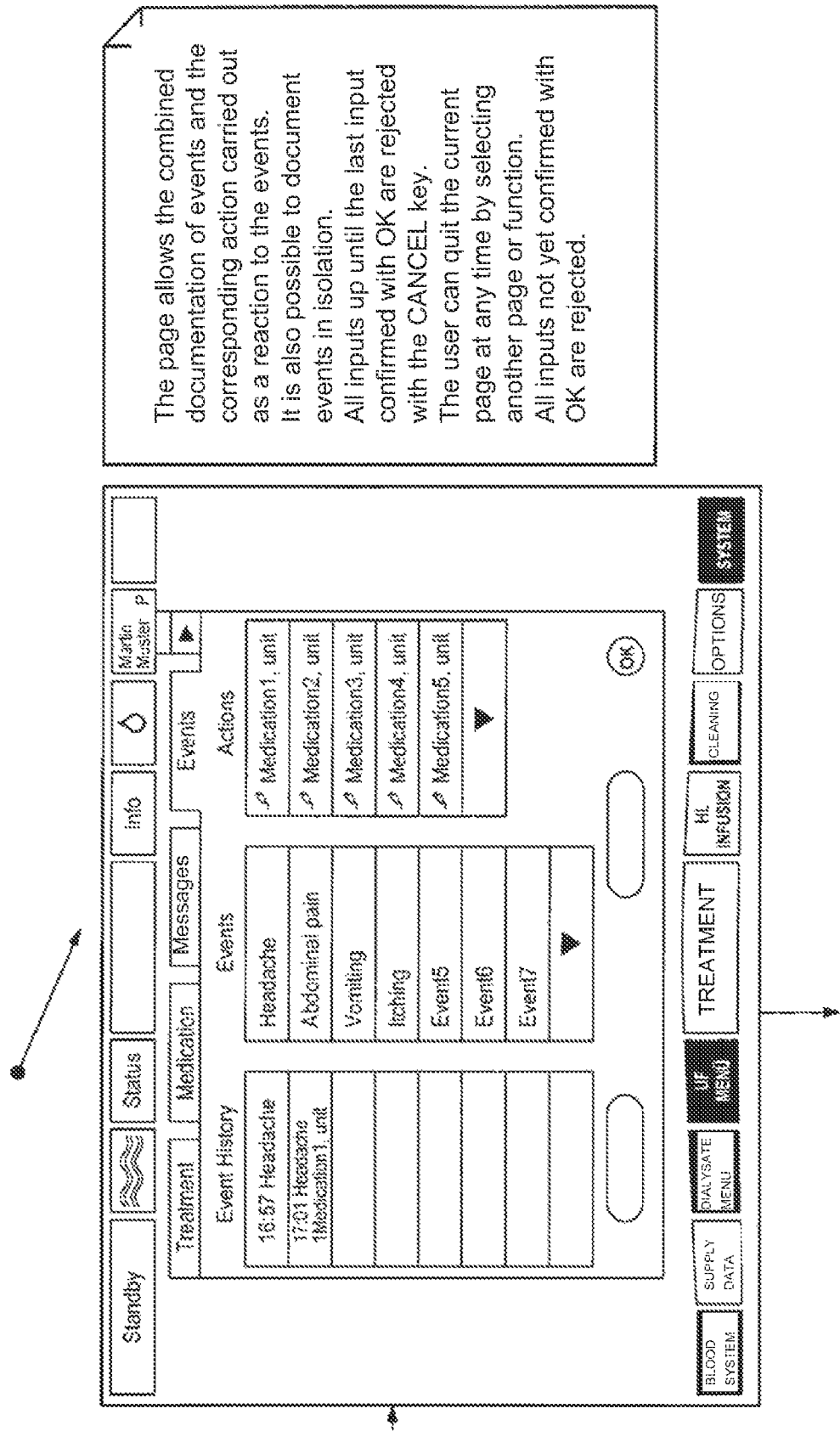
FIGS. 4A to 4G show the central display area of the screen surface in patient mode, wherein the event page is called.
Figure 4B:
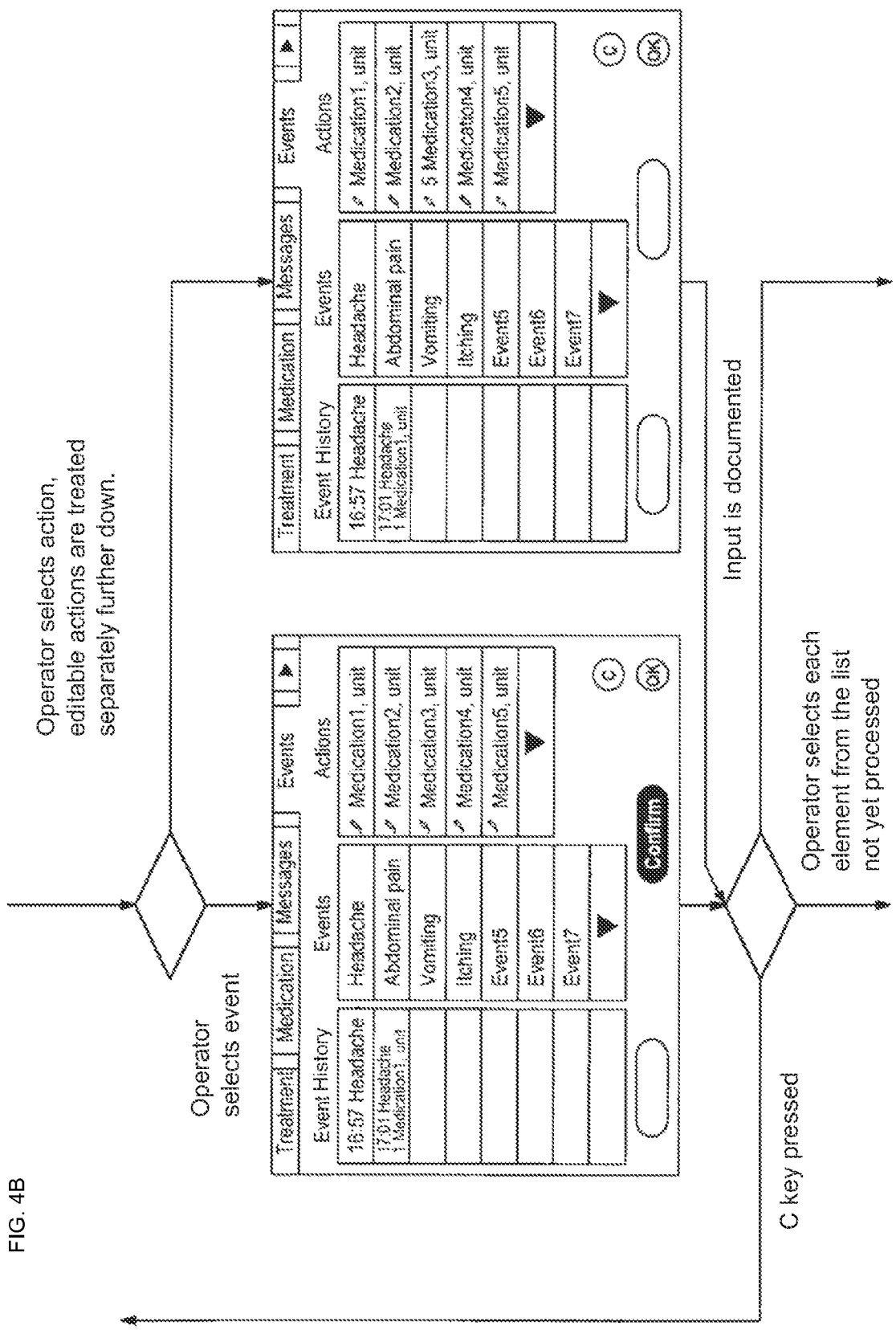
Figure 4C:
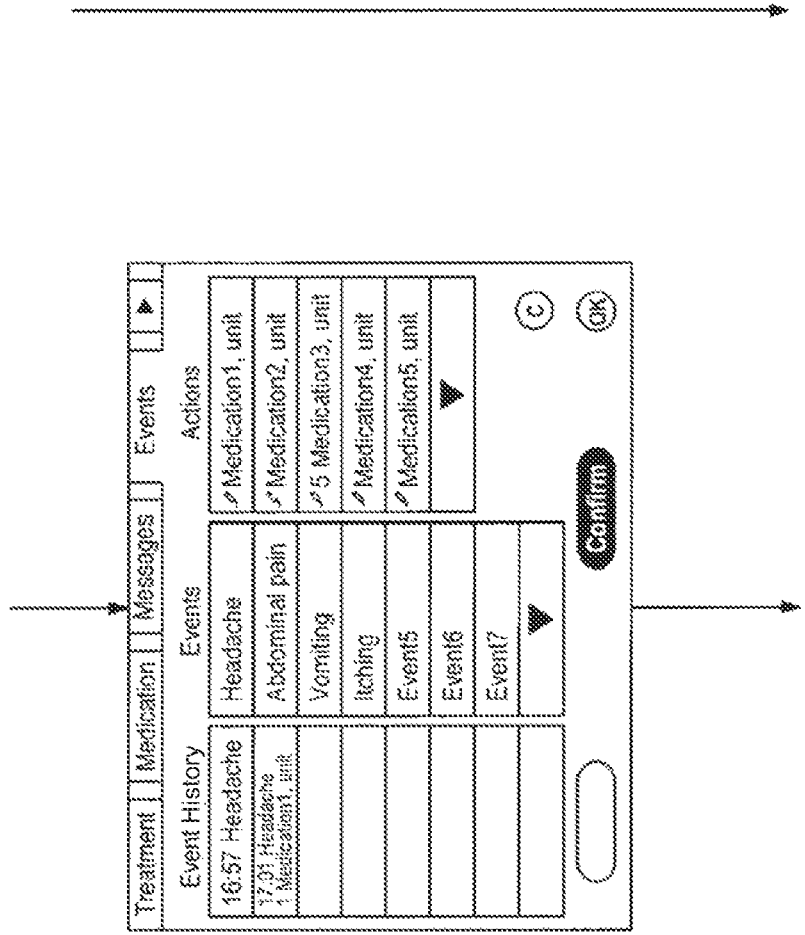
Figure 4D:
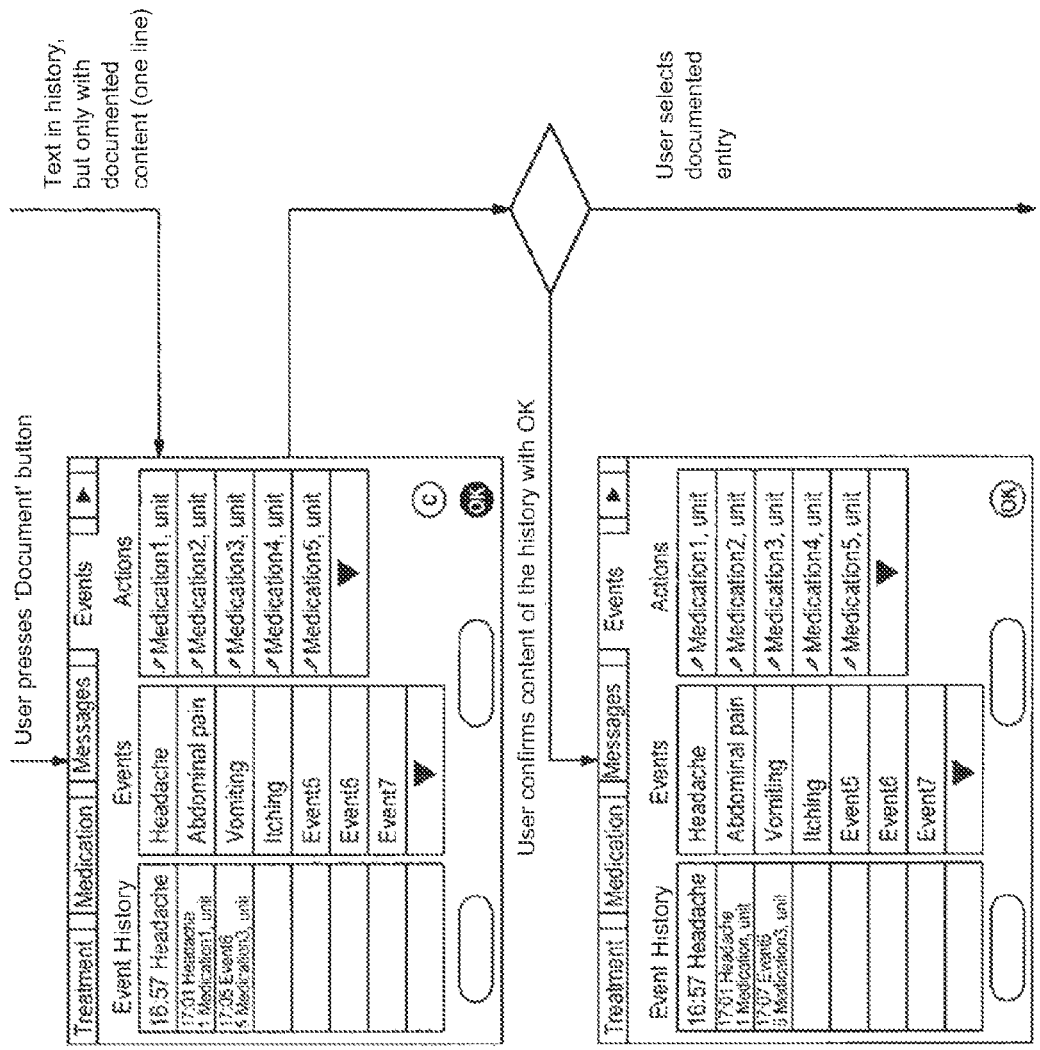
Figure 4E:
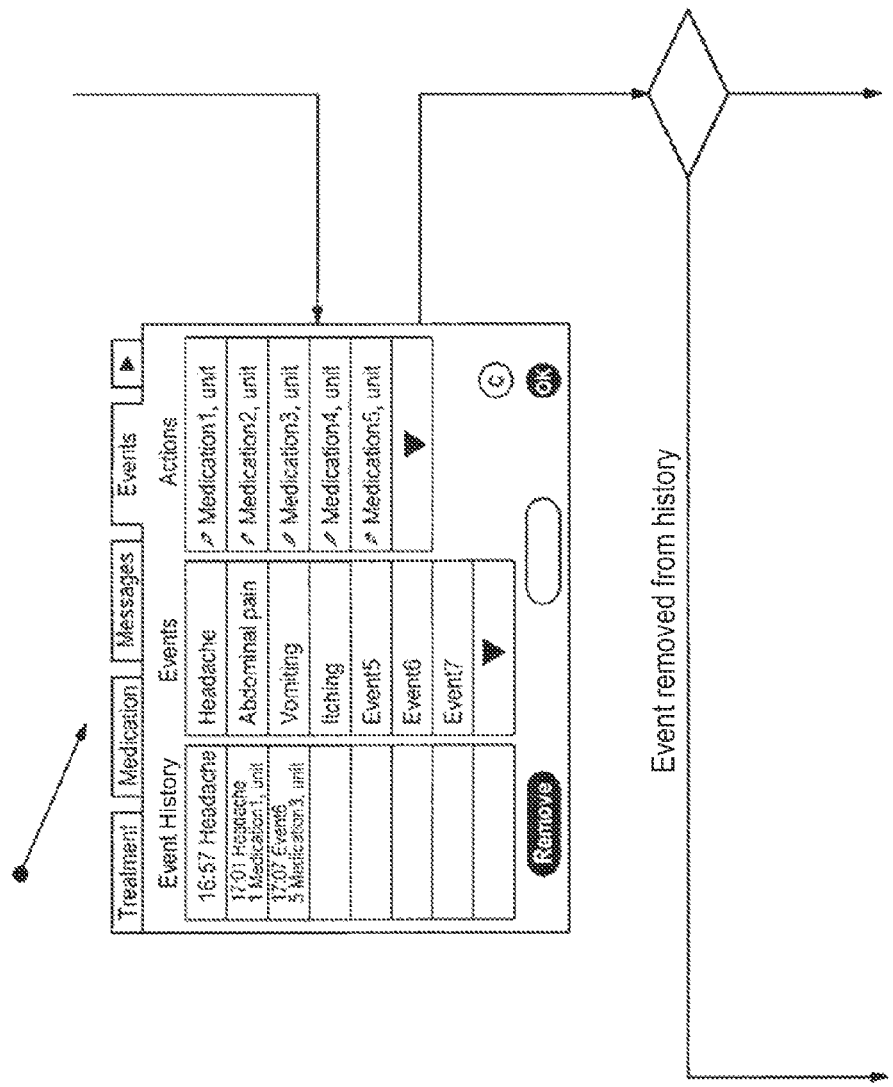
Figure 4F:
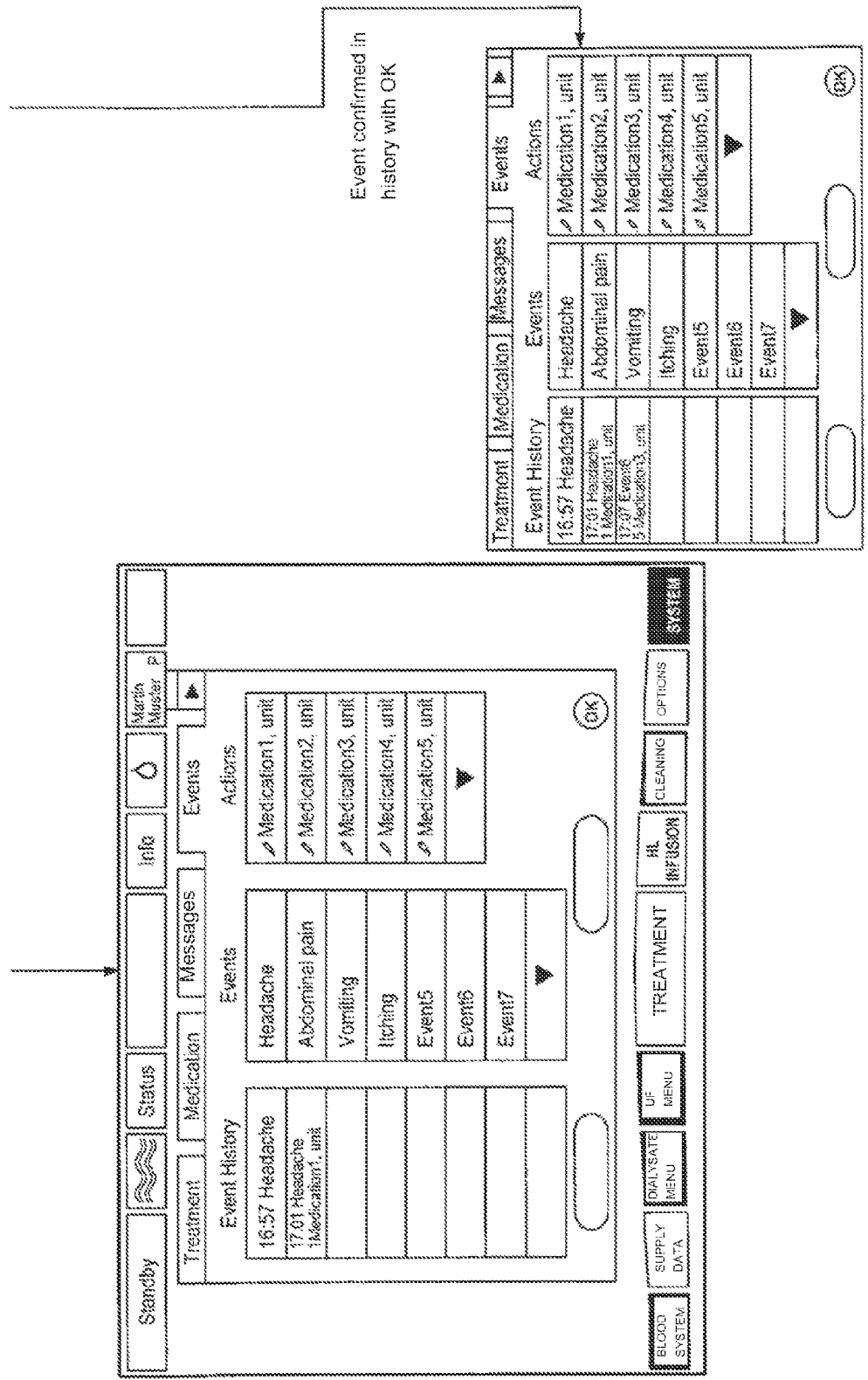
Figure 4G:
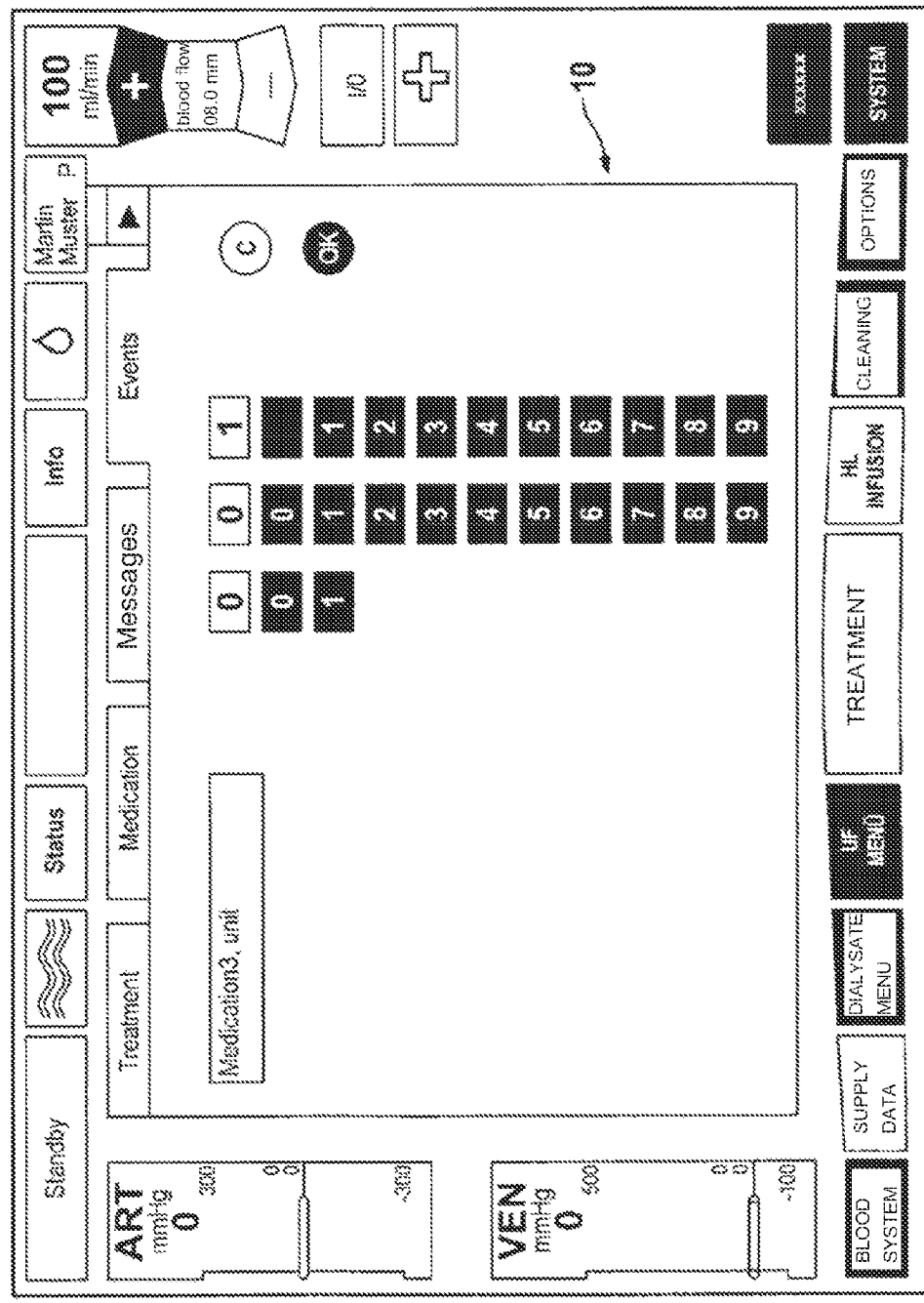
Figure 5A:
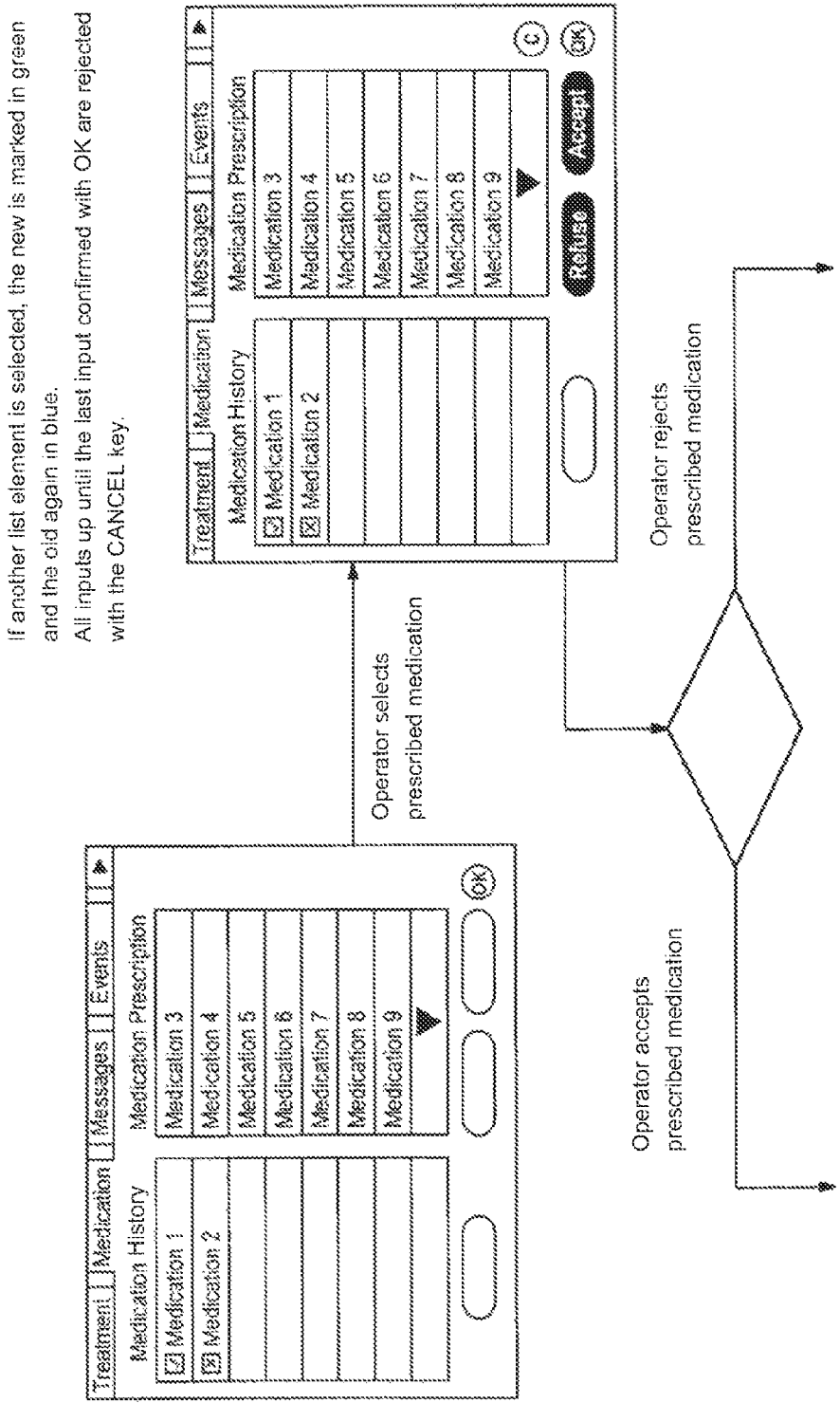
FIGS. 5A to 5E show a flow chart for explaining the logical sequence of the operation after calling up the medication page.
Figure 5B:
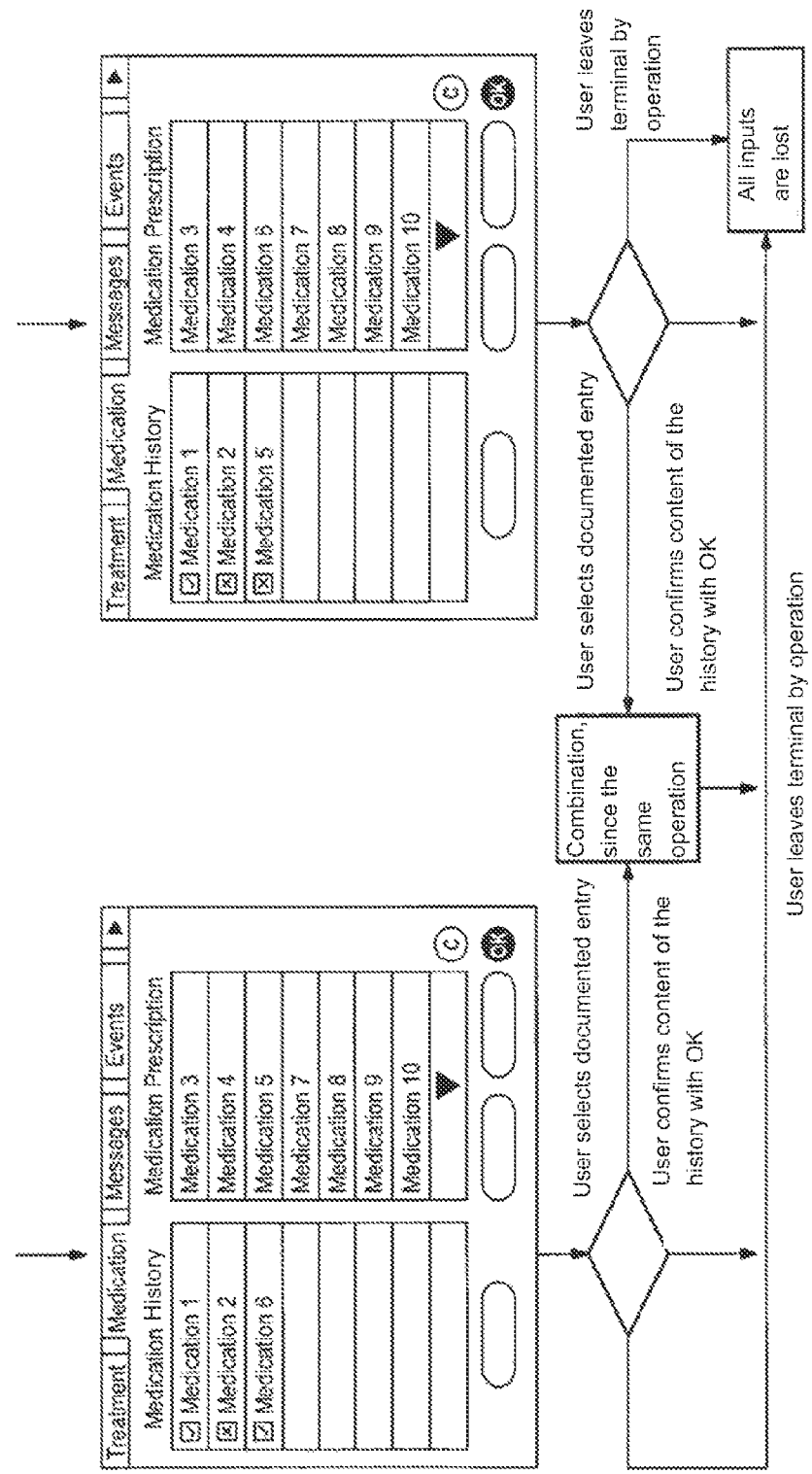
Figure 5C:
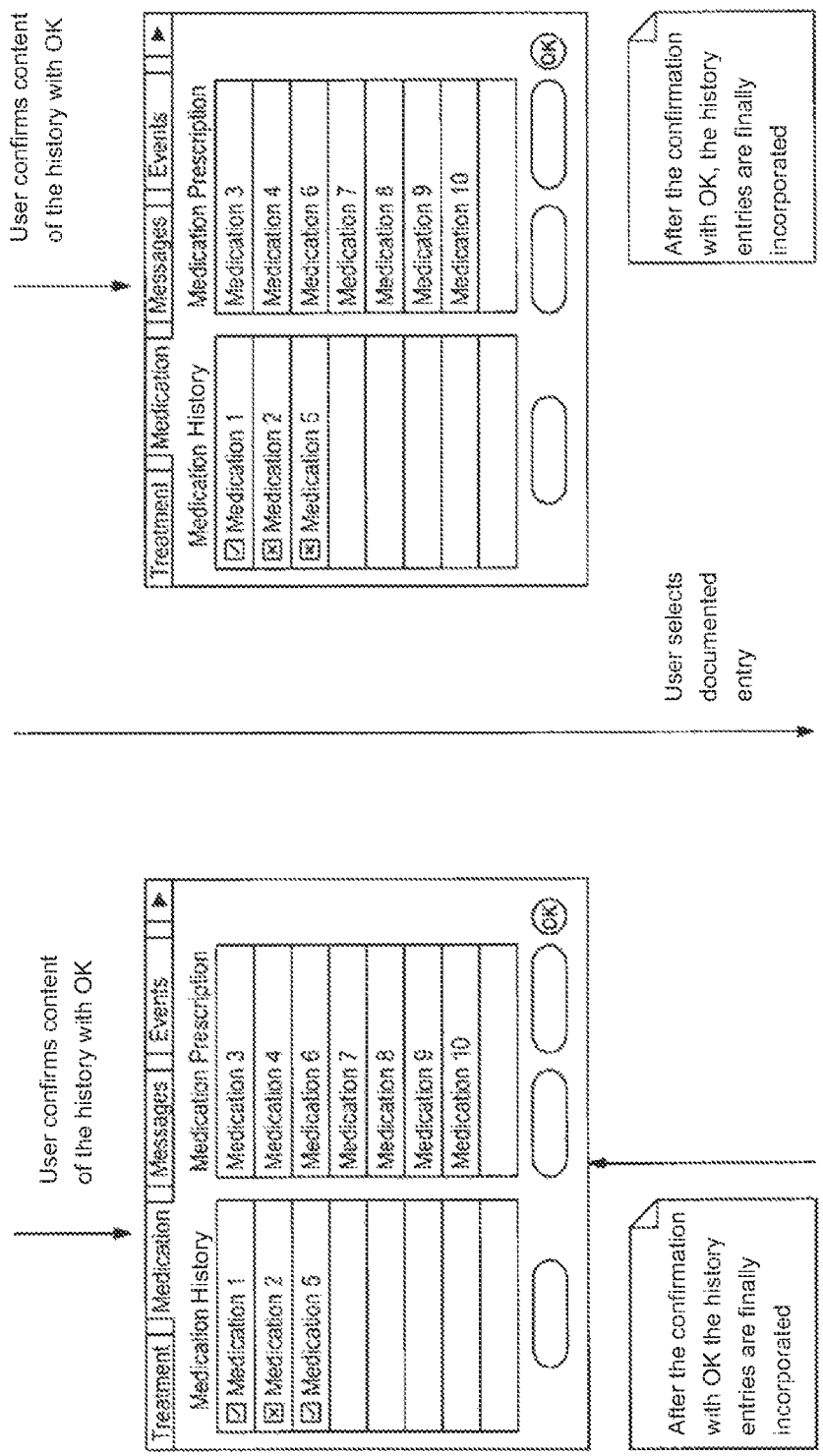
Figure 5D:
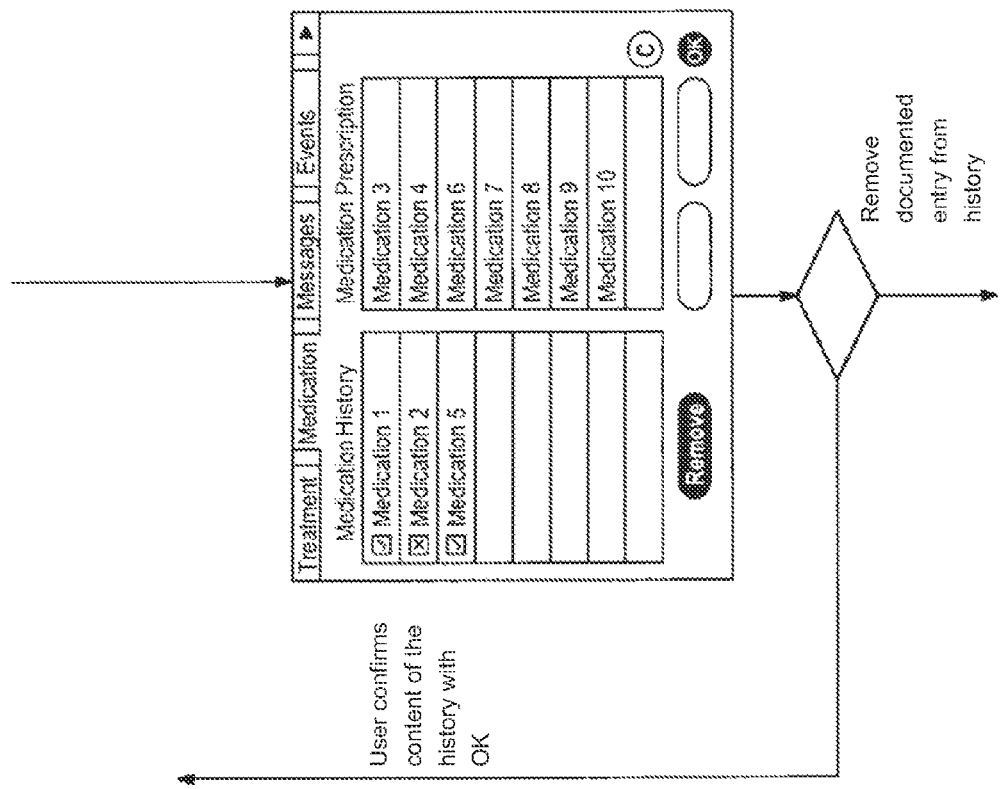
Figure 5E:
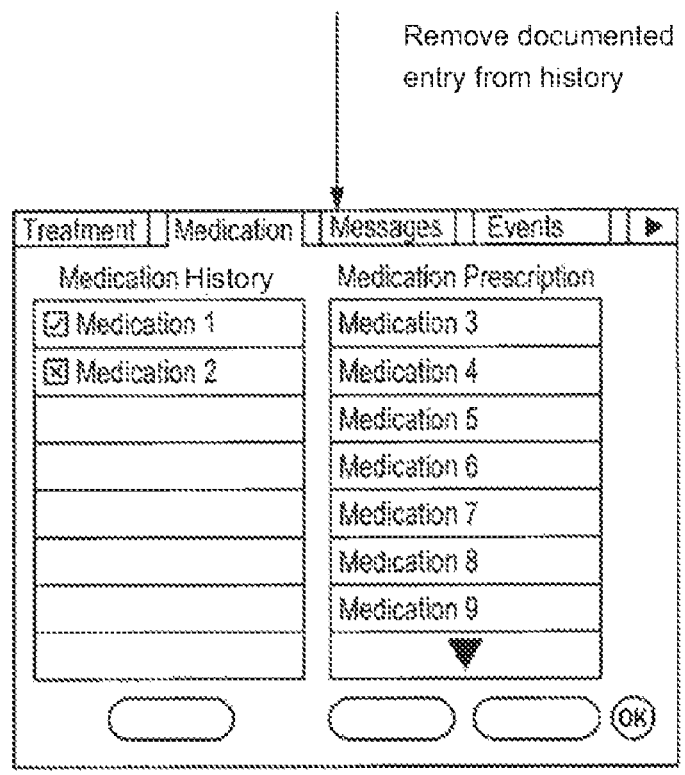

The patient-related data defines graphic elements which can be displayed on the screen. FIG. 3 shows the screen surface in the patient mode. The graphic elements can be positioned by the server anywhere within central display area 10 (FIG. 2). Before the patient-related data appears on the screen in the patient mode, it is determined whether a display of the individual graphic elements is possible within the predetermined limits of the central display area 10 without overlapping elements already displayed. If this is the case, the display of the elements is prevented. Otherwise, the elements appear in the central display area of the screen. This ensures that there is no display until all the relevant information is available, thus excluding the possibility of misinterpretation of the displayed contents.

The graphic elements are first positioned virtually according to the position information in the HTML page description. Here it is determined, for each element, whether the position has not already been reserved for another element and whether the element lies fully within the central display area. Not until then is the position for this element released. However, if the position is already occupied, the page is not displayed and an error message appears on the page. In this case, the rest of the screen remains operable. Not until all the elements have been positioned successfully and virtually without collision is the complete page displayed.

To avoid malfunctions, only the graphic elements which are known to the dialysis devices are displayed on the screen, for which purpose the HTML elements are provided with a so-called class attribute. Before the individual elements are displayed on the screen it is determined whether the elements are provided with a class attribute. In this case, only the elements which are provided with a class attribute are displayed. On the other hand, elements without a class attribute are ignored. If the server is provided with a more recent software version than one of the dialysis devices, elements with unknown class attributes could be available. These elements with unknown class attributes are not displayed, preventing malfunctions. However, the user is alerted.

In the patient mode, different groups of patient-related data are displayed on different pages. The different groups include, for example, the treatment carried out, the prescribed medications, messages, and events or actions. The individual pages can be called with the finger by pressing the corresponding button on the upper edge of the pages. FIG. 3 shows the event page. Each page contains a plurality of data sets which include, on the event page, for example, the prescribed medications, e.g. Medication 1, Medication 2, Medication 3, etc., or different events, e.g. headaches, etc. These data sets are grouped into individual lists 16, 17, 18. If an event occurs during the treatment, the event can be documented with the time and an appropriate action by selecting the appropriate button.

The menu selection for the display and documentation of events and actions is described in further detail in the following with reference to FIGS. 4A to 4G. For example, the operator selects "Event 6" from the event list 17 of different predetermined events. This text is then highlighted, for example in green. Instead of an event the operator may now also select an action. If the operator has first selected an event, an action can now be selected.

For example, the operator selects the action "Medication 3, unit" from action list 16, thus the administration of a certain medication is selected from the list of medications. The operator then opens a new page (FIG. 4G) on which the number of units administered is entered. For example, the operator enters 5 units by pressing the corresponding button 5. The operator then returns to the previous page. The action "5 Medication 3, unit", is now highlighted, for example in green. The entered data set "5" has been assigned to the selected data set "Medication 3, unit".

After the inputs are confirmed the selected events and actions are displayed in a list 18 of stored events (Event History), with indication of the time of input (17:07). The text is given a colored background, for example blue. The operator can confirm this display by pressing the "OK" button. The text is now underlined, for example in grey. It is also possible to remove the events and actions shown in the "Event History" from the "History" by pressing the "Remove" button.

The patient mode therefore allows the assignment of certain events and certain actions to be selected, which can be stored in sequence for documentation. Here the data sets are stored in server 2, independently of the individual dialysis devices 1, 1', 1". The operator is therefore informed of the events and actions that have already taken place before new events and actions are selected. For example, it is indicated to the operator, before he inputs the event "Event 6" and the action "5 Medication 3, unit", that the patient already had headaches and that medication 1 was already administered. The combination of the individual data sets from which the operator may make a selection, and the documentation of the data sets, increases the safety of the dialysis treatment.

If the operator selects the "Medications" page from among the different groups of patient-related data, a new page appears. FIGS. 5A to 5E show a flow chart to explain the logical sequence of the operation after the "Medications" page is called. The operator may make a further selection from within this group under a plurality of data sets. For example, the operator may select the desired medication, for example, Medication 3, Medication 4, or Medication 5, from the list of available medications loaded on the device to supply patient-related data. The text of the selected medication is now highlighted, for example in green. The operator may now accept or reject the selected prescribed medication by pressing the "Reject" or "Accept" button. If the operator accepts the medication selected, the medication is displayed under the list labeled "Medication History" and identified with a checkmark. If the operator rejects the medication selected, the medication is displayed under the list labeled "Medication History" and identified by an "x".

After confirmation with "OK", all entries in the "Medication History" list are taken over for documentation and stored in server 2, independently of the dialysis device. On the other hand, if the user quits the patient mode, all the selected inputs will be lost. If the "Medication" page is called again later, the patient-related data sets are loaded so the user is able to follow the progress of the treatment. For example, the user can see from the information displayed that medications 1 and 5 have been administered but medication 2 has not.

Figure 6A:
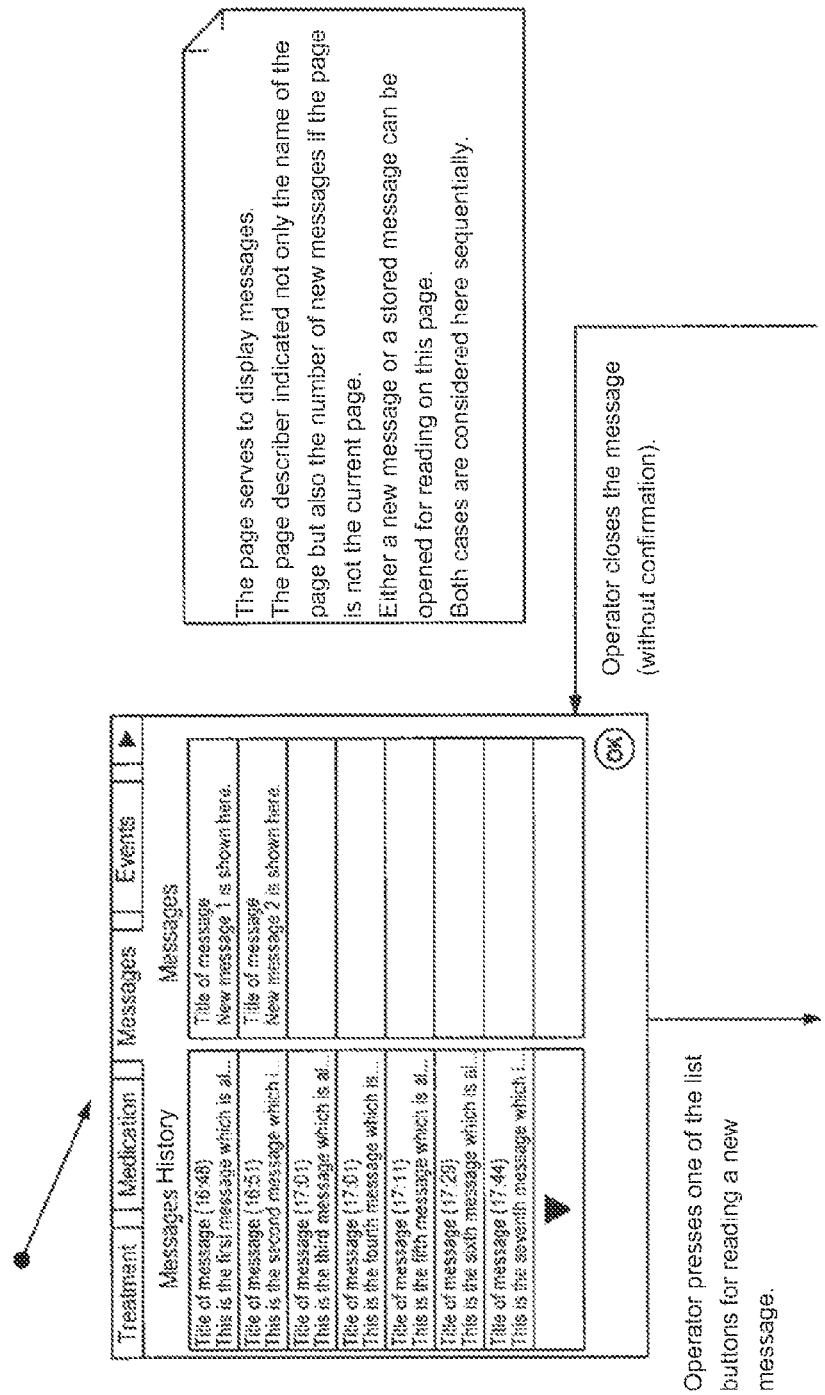
FIGS. 6A and 6C show a flow chart for explaining the logical sequence of the operation after calling up the message page.
Figure 6B:
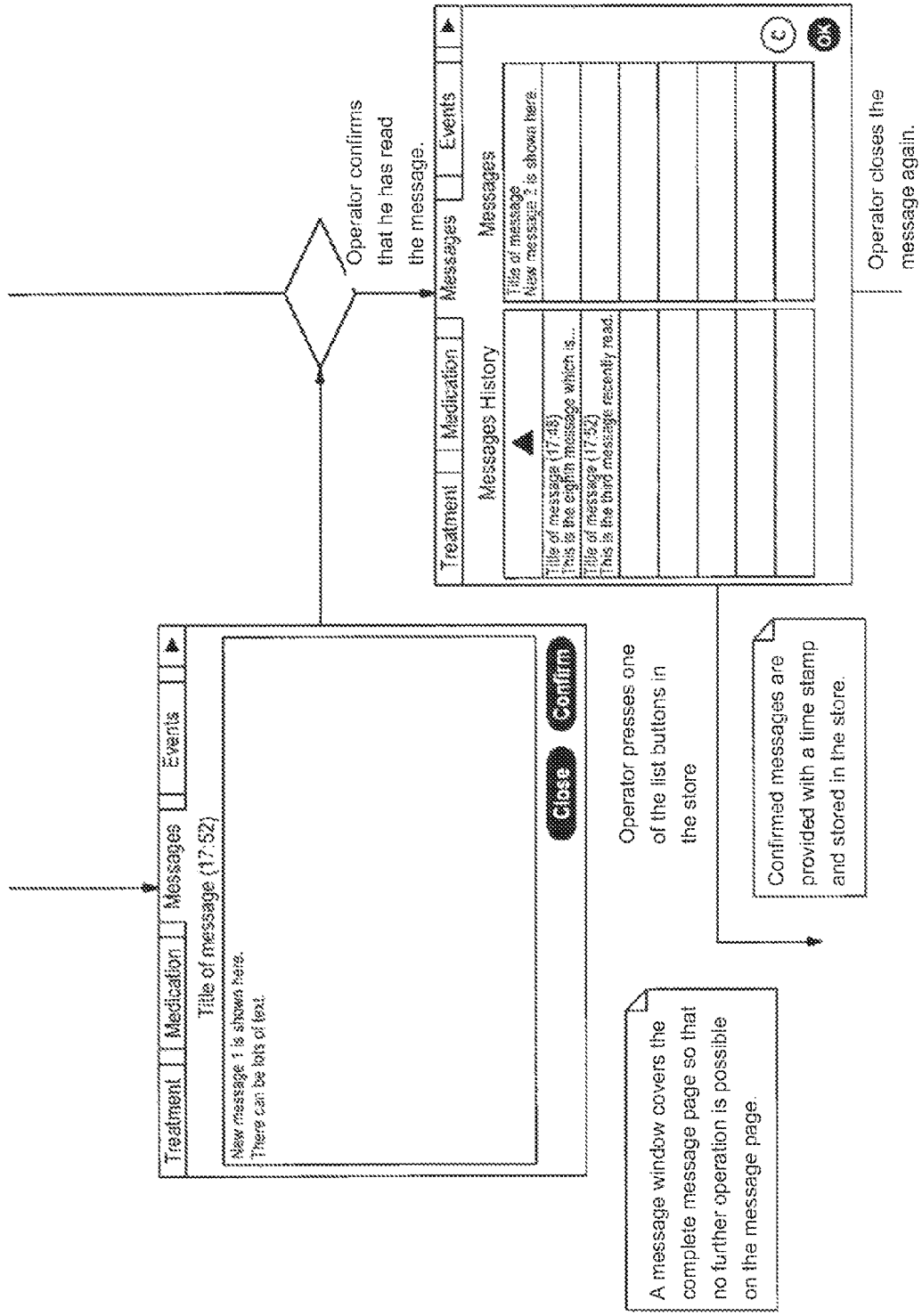
Figure 6C:
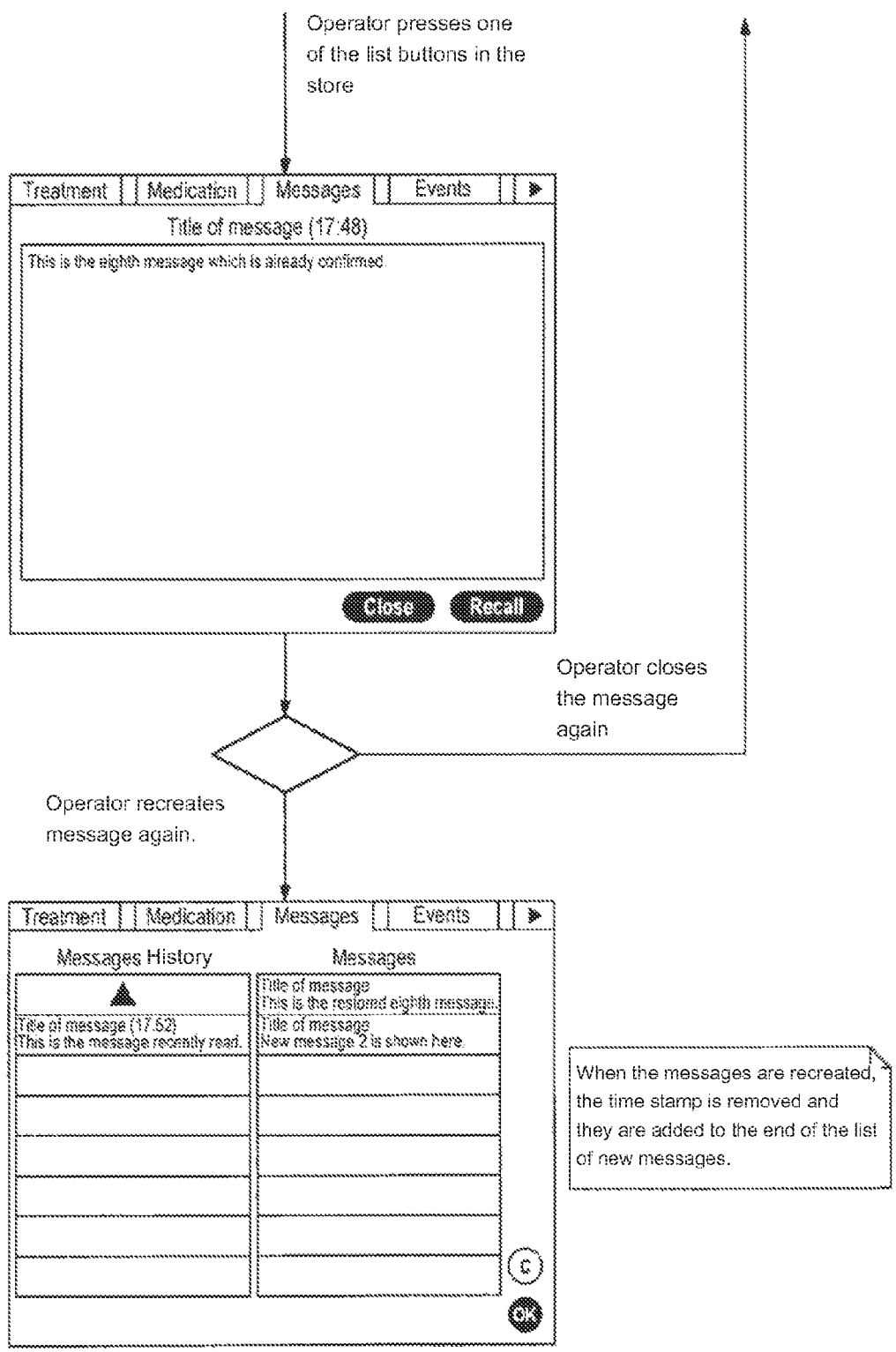

In addition to the display and documentation of events and actions, as well as the administration of medications, the server also makes patient-related messages available to the user of the individual dialysis devices. Messages can be stored in the dialysis system for each patient. These messages are entered centrally using the input device 2B of the device for supplying the patient-related data. For example, the messages are entered with a keyboard or read in on a data carrier. The messages may also be made available by other external devices not shown, which communicate with the server. FIGS. 6A to 6C show a flow chart to explain the logical sequence of the operation.

When the treatment mode is called, the patient button 15 flashes in status bar 11 when new messages are received. The operator may then activate the patient menu and select the "Messages" page. To read the messages, the operator presses a button displaying the title of the message, which opens a new page displaying the text of the messages with an indication of the time they were entered. By pressing the "Confirm" button the operator confirms reading the message. Otherwise, the operator closes the page by pressing the "Close" button.

After the operator confirms reading the message, the title of the message in the list of messages disappears. The title of the message now appears in the "Message History" list, with an indication of the time at which the user read the message. All the previously read messages also appear in the list. The operator can now open more unread messages, in sequence, and can store them for documentation with an indication of the time.

To avoid errors in documentation, all the contents of the pages are called several times, preferably at least three times, by the server and represented in different operating stages before they can be stored in the data bank of the server. The embodiments show that each element must first be selected, the selection then confirmed and the confirmed selection will finally be incorporated in the "History" list. The risk of incorrect inputs is thus reduced by the multiple confirmation stages.

The invention claimed is:

1. A medical treatment system comprising:
at least one medical treatment device comprising: a central control unit, and an input/display device for entering and displaying patient-related data and machine-related data to control the at least one medical treatment device; and a device for supplying patient-related data comprising a storage device for storing patient-related data;

the input/display device comprising a plurality of means for entering and displaying different groups of patient-related data, each means for entering and displaying a group of patient-related data comprising:

means for displaying a plurality of patient-related data sets;

means for selecting one or more patient-related data sets from the plurality of patient-related data sets; and means for displaying one or more of the selected patient-related data sets, wherein the input/display device has a treatment mode and a patient mode, wherein machine-related data sets can be displayed in the treatment mode and patient-related data sets can be displayed in the patient mode, wherein the at least one medical treatment device and the device for supplying patient-related data interact to allow the patient-related data entered with the input/display device to be stored in the storage device and the patient-related data stored in the storage device to be displayed with the input/display device, wherein the selected patient-related data sets are stored within the storage device to provide a documentation of a treatment session.

2. The medical treatment system of claim 1, wherein means for entering and displaying a group of patient-related data further comprises: means for entering one or more new patient-related data sets, and wherein means for selecting one or more patient-related data sets interact with means for entering one or more patient-related data sets to add the new patient-related data sets to the plurality of patient-related data sets that can be selected and displayed.

3. The medical treatment system of claim 1, wherein the input/display device is designed such that machine-related data sets and the patient-related data sets can both be displayed in the patient mode.

4. The medical treatment system of claim 1, wherein the input/display device is designed such that a machine-related display area for displaying machine-related data sets is only defined in the treatment mode.

5. The medical treatment system of claim 4, wherein the input/display device is designed such that a patient-related display area for displaying patient-related data sets is defined in the patient mode.

6. The medical treatment system of claim 5, wherein the machine-related display area is distinct from the patient-related display area.

7. The medical treatment system of claim 1, wherein the device for supplying patient-related data further comprises a device for entering patient-related data.

8. The medical treatment system of claim 1, wherein the medical treatment system comprises a plurality of treatment devices, the plurality of treatment devices and the device for supplying patient-related data being connected to each other to form a network.

9. The medical treatment system of claim 1, wherein the input/display device further comprises a screen for displaying patient-related data.

10. The medical treatment system of claim 9, wherein the screen is a touch screen.

11. The medical treatment system of claim 1, wherein the input/display device further comprises a screen for displaying patient-related data, and the means for entering and displaying different groups of patient-related data are pages with individually selectable fields represented on the screen.

12. The medical treatment system of claim 1, wherein the at least one medical treatment device is an extracorporeal blood treatment device.

13. A medical treatment system comprising:

at least one medical treatment device comprising: a central control unit, and an input/display device for entering and displaying patient-related data and machine-related data to control the at least one medical treatment device; and a device for supplying patient-related data comprising a storage device for storing patient-related data;

the input/display device being designed to display machine-related data in a treatment mode and patient-related data in a patient-related display area in a patient mode, the input/display device comprising:

means for determining whether the patient-related data can be represented within the patient-related display area without overlapping data already displayed, and means for preventing the display of the patient-related data when the patient-related display area is exceeded or when there is an overlap of data, wherein the at least one medical treatment device and the device for supplying patient-related data interact to allow the data entered with the input/display device to be stored in the storage device and the data stored in the storage device to be displayed with the input/display device.

14. The medical treatment system of claim 13, wherein the input/display device is designed such that machine-related data and patient-related data can both be displayed in the patient mode.

15. The medical treatment system of claim 13, wherein the input/display device is designed such that a machine-related display area exclusively for displaying machine-related data is defined in the treatment mode.

16. The medical treatment system of claim 15, wherein the machine-related display area is distinct from the patient-related display area.

17. The medical treatment system of claim 13, wherein the device for supplying patient-related data further comprises a device for inputting patient-related data.

18. The medical treatment system of claim 13, wherein the medical treatment system comprises a plurality of treatment devices, wherein the plurality of treatment devices and the device for supplying patient-related data are connected to each other to form a network.

19. The medical treatment system of claim 13, wherein the input/display device further comprises a screen for displaying the patient-related data.

20. The medical treatment system of claim 19, wherein the screen is a touch screen.

21. The medical treatment system of claim 13, wherein the at least one medical treatment device is an extracorporeal blood treatment device.

22. A medical treatment system comprising:

at least one medical treatment device comprising: a central control unit, and an input/display device for entering and displaying patient-related data and machine-related data to control the at least one medical treatment device; and a device for supplying patient-related data comprising a storage device for storing patient-related data;

the input/display device being designed to display machine-related data in a treatment mode and patient-related data exclusively in a patient-related display area in a patient mode, the input/display device comprising:

means for cyclic interrogation of patient-related data that indicate when new patient-related data are supplied by the device for supplying patient-related data, and an indication of the new patient-related data is displayed in the treatment mode, wherein the at least one medical treatment device and the device for supplying patient-related data interact to allow the data entered with the input/display device to be stored in the storage device and the data stored in the storage device to be displayed with the input/display device.

23. The medical treatment system of claim 22, wherein the input/display device is designed such that machine-related data and patient-related data can both be displayed in a patient mode.

24. The medical treatment system of claim 22, wherein the input/display device is designed such that a machine-related display area exclusively for displaying machine-related data is defined in the treatment mode.

25. The medical treatment system of claim 24, wherein the machine-related display area is distinct from the patient-related display area.

26. The medical treatment system of claim 22, wherein the input/display device is designed such that the patient-related display area exclusively for displaying patient-related data sets is only defined in the patient mode.

27. The medical treatment system of claim 22, wherein the device for supplying patient-related data further comprises a device for inputting patient-related data.

28. The medical treatment system of claim 22, wherein the medical treatment system comprises a plurality of treatment devices, wherein the plurality of treatment devices and the device for supplying patient-related data are connected to each other to form a network.

29. The medical treatment system of claim 22, wherein the input/display device further comprises a screen for displaying the patient-related data.

30. The medical treatment system of claim 29, wherein the screen is a touch screen.

31. The medical treatment system of claim 22, wherein the at least one medical treatment device is an extracorporeal blood treatment device.

32. The medical treatment system of claim 22, wherein the indication of new patient-related data comprises a patient button located in a status bar in the treatment mode.

* * * * *